(12) United States Patent
Gomez-Godinez et al.

(10) Patent No.: US 11,479,748 B2
(45) Date of Patent: Oct. 25, 2022

(54) METHODS AND DEVICE FOR STIMULATING DNA REPAIR

(71) Applicant: The Regents of the University of California, Oakland, CA (US)

(72) Inventors: Veronica Gomez-Godinez, La Jolla, CA (US); Michael Berns, La Jolla, CA (US); Shirli Cohen, La Jolla, CA (US); Matthew Ono, La Jolla, CA (US); Daryl Preece, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 156 days.

(21) Appl. No.: 16/833,238

(22) Filed: Mar. 27, 2020

(65) Prior Publication Data

US 2020/0308526 A1    Oct. 1, 2020

Related U.S. Application Data (60) Provisional application No. 62/825,449, filed on Mar. 28, 2019.

(51) Int. Cl.
| | | |
|---|---|---|
| C12M 1/42 | (2006.01) | |
| C12M 1/00 | (2006.01) | |
| B01L 7/00 | (2006.01) | |
| B01L 3/00 | (2006.01) | |

(52) U.S. Cl.
CPC ......... *C12M 35/02* (2013.01); *B01L 3/50273* (2013.01); *B01L 7/52* (2013.01); *C12M 29/00* (2013.01); *C12M 31/10* (2013.01); *C12M 35/08* (2013.01)

(58) Field of Classification Search
CPC ...... C12M 35/02; C12M 35/08; C12M 31/10; B01L 3/50273; B01L 7/52; B01L 7/00
See application file for complete search history.

(56) References Cited

U.S. PATENT DOCUMENTS

| | | |
|---|---|---|
| 9,440,092 B2 | 9/2016 | Tapper et al. |
| 9,561,385 B2 | 2/2017 | Tapper et al. |
| 9,731,143 B2 | 8/2017 | Tapper et al. |
| 9,744,377 B2 | 8/2017 | Tapper et al. |
| 9,744,378 B2 | 8/2017 | Tapper et al. |
| 9,764,156 B2 | 9/2017 | Tapper et al. |
| 9,789,333 B2 | 10/2017 | Tapper et al. |
| 9,814,905 B2 | 11/2017 | Tapper et al. |
| 9,962,545 B2 | 5/2018 | Asah |
| 9,968,799 B2 | 5/2018 | Johnson et al. |
| 9,999,783 B2 | 6/2018 | Tapper et al. |
| 10,004,919 B2 | 6/2018 | Lemmens et al. |
| 10,022,554 B2 | 7/2018 | Tapper et al. |
| 10,022,555 B2 | 7/2018 | Tapper et al. |
| 10,039,600 B2 | 8/2018 | Khormaei et al. |
| 10,052,496 B2 | 8/2018 | Sauer |

(Continued)

OTHER PUBLICATIONS

Kim, et al., "A Protective Mechanism of Visible Red Light in Normal Human Dermal Fibroblasts: Enhancement of GADD45A-Mediated DNA Repair Activity", Journal of Investigative Dermatology (2017), vol. 137, pp. 466-474.

*Primary Examiner* — Michael L Hobbs
(74) *Attorney, Agent, or Firm* — Foley & Lardner LLP (57) ABSTRACT

A device for DNA repair phototherapy is provided. A method of use for the device to provide DNA phototherapy to damaged DNA is also disclosed.

21 Claims, 9 Drawing Sheets

(56) References Cited

U.S. PATENT DOCUMENTS

| | | | |
|---|---|---|---|
| 2002/0173833 A1* | 11/2002 | Korman | A61K 41/0071 |
| | | | 607/88 |
| 2007/0292941 A1* | 12/2007 | Handique | F16K 99/003 |
| | | | 435/288.7 |
| 2010/0267126 A1* | 10/2010 | Jacobs | C12M 31/10 |
| | | | 47/17 |
| 2014/0011245 A1* | 1/2014 | Flynn | C12M 21/02 |
| | | | 362/249.02 |
| 2019/0317116 A1* | 10/2019 | Phelan | G01N 35/00623 |

\* cited by examiner

METHODS AND DEVICE FOR STIMULATING DNA REPAIR

CROSS-REFERENCE TO RELATED APPLICATION

This application claims priority under 35 U.S.C. § 119(e) to U.S. Provisional Application No. 62/825,449 filed Mar. 28, 2019, the content of which is incorporated by reference into this disclosure in its entirety.

FEDERAL FUNDING STATEMENT

This invention was made with government support under FA9550-17-1-0193 awarded by the Air Force Office of Scientific Research. The government has certain rights in the invention.

BACKGROUND

Red light exposure can have phototherapeutic effects on skin cells and other biological cells and tissues affected by UV damage. However, existing methods and devices using red light in DNA phototherapy have not identified the proper duration, intensity, or delivery mechanisms for optimal DNA repair. If the radiant intensity of the red light is too low, then exposure is inadequate and the repair biomarkers are not activated. Conversely, prolonged exposure to excessive electromagnetic radiation only furthers DNA damage. Moreover, in the context of skin treatment, excessive radiant intensity can burn tissue or have carcinogenic side effects.

Thus, there is a need for a device and methods of use that provide safe, effective, and targeted red light DNA phototherapy.

SUMMARY

Figure 1:
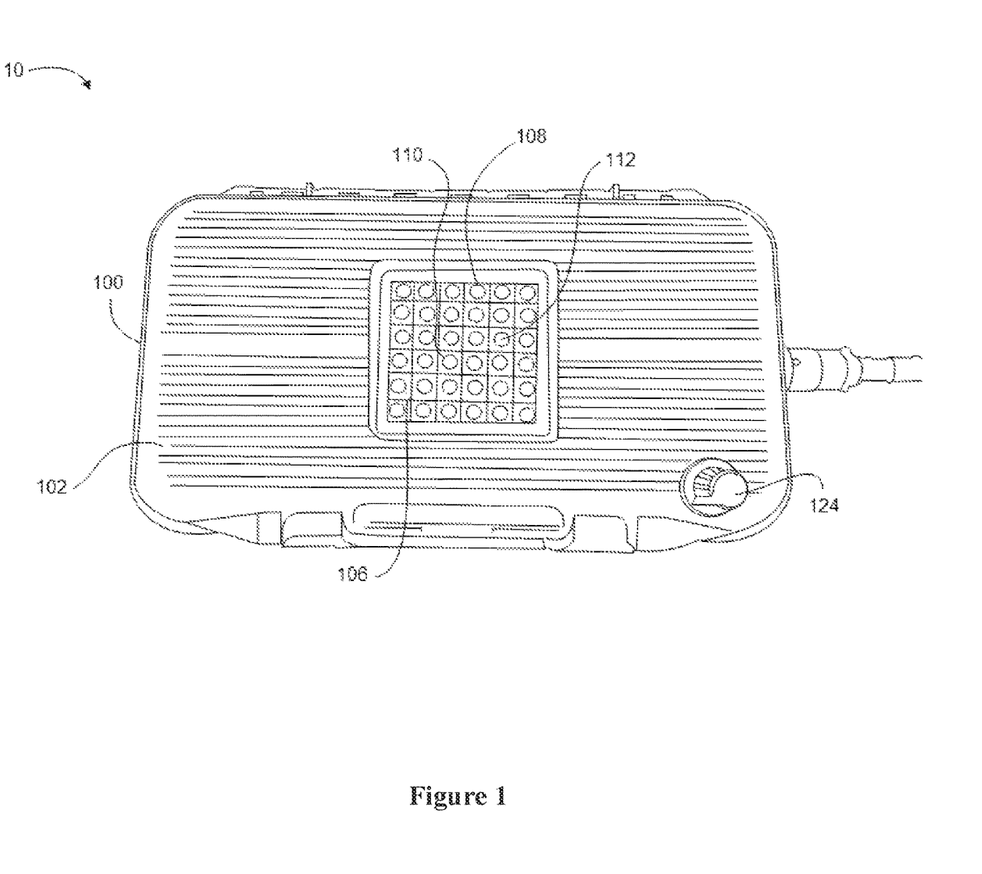
FIG. 1 shows a top view of a DNA repair device in accordance with the principles of the present disclosure.
Figure 2:
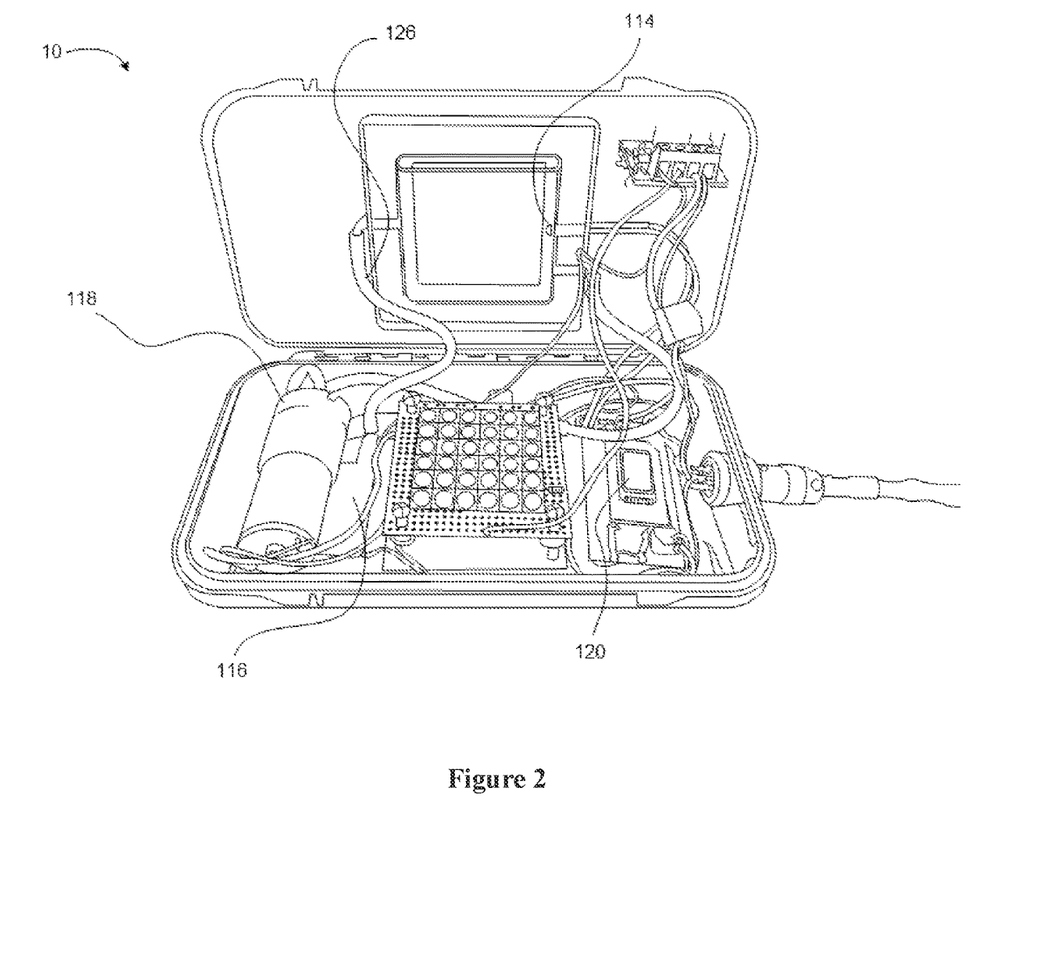
FIG. 2 shows an expanded cross-sectional view of a DNA repair device in accordance with the principles of the present disclosure.
Figure 6:
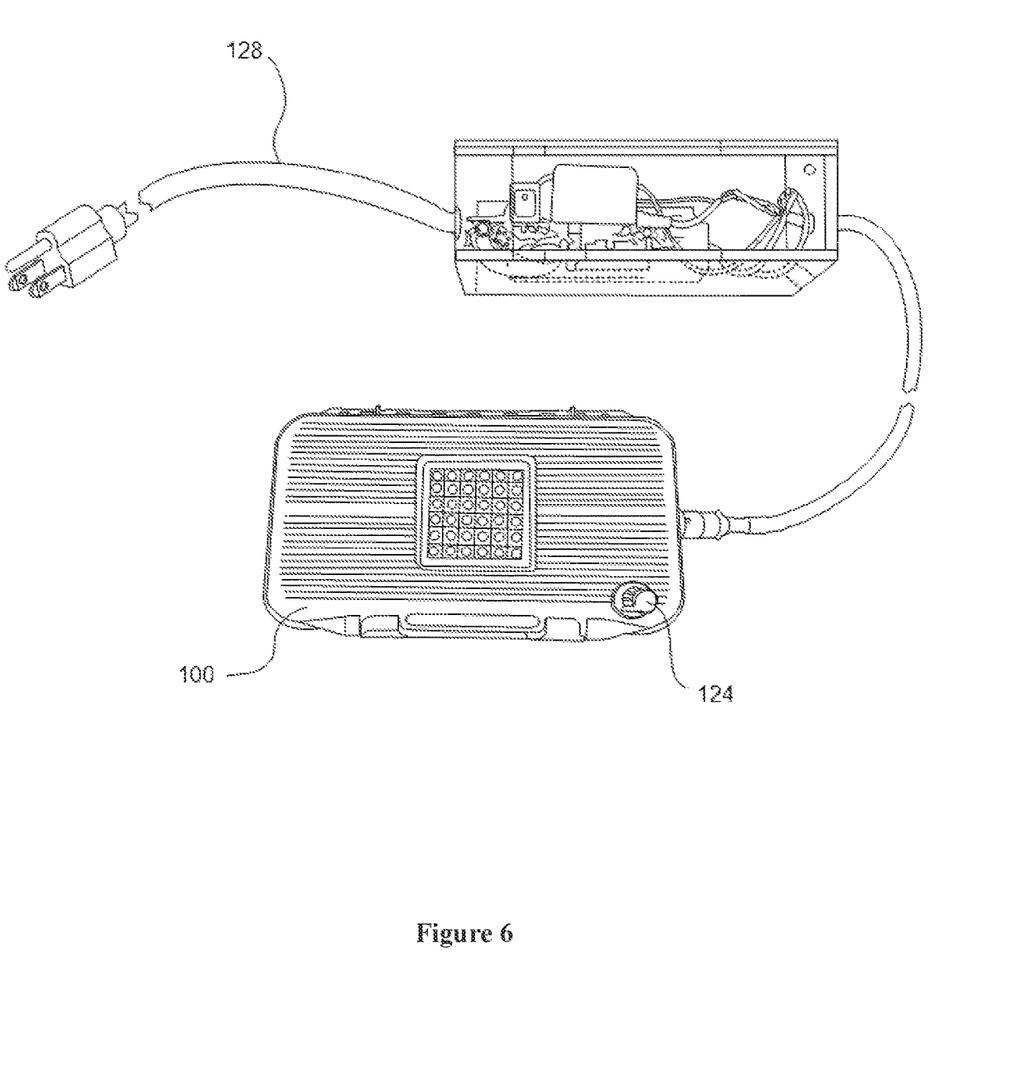
FIG. 6 shows a top view of a DNA repair device in accordance with the principles of the present disclosure with accompanying power supply.

The present disclosure overcomes the drawbacks of previously-known devices and methods by providing a DNA repair device. In some embodiments, the DNA repair device comprises, or consists essentially of, or yet further consists of a housing that in turn comprises at least a top side, wherein the top side of the housing comprises: an opening; a fillable, translucent platform coupled to the top side of the housing, wherein the platform is situated between the opening and an array disposed within the housing, wherein the array comprises a plurality of electromagnetic energy sources; a thermal sensor coupled to the platform; a heat exchanger disposed within the housing and operatively coupled to a fluid pump, wherein the heat exchanger is configured to heat or cool a medium in the fluid pump, further wherein the fluid pump is configured to circulate the medium to the fillable platform; and a control circuit disposed within the housing and operatively coupled to at least one of the thermal sensor, the array, the heat exchanger, and the fluid pump. FIGS. 1, 2, and 6 are exemplification of the DNA repair device of this disclosure.

Alternatively or additionally, in some embodiments, the control circuit comprises, or consists essentially of, or yet further consists of a programmable input device. In one aspect, the input device is controlled by a user-activated tunable knob. FIG. 1 exemplifies this aspect.

In a further aspect, the fluid pump comprises, or consists essentially of, or yet further consists of a circulation loop in fluid communication with the fillable platform. FIG. 2 exemplifies this aspect.

Non-limiting examples of the electromagnetic energy sources of the device include, for example at least one of a light-emitting diode, an organic light emitting diode, a laser, or a fluorescent lamp. In one aspect, the electromagnetic energy source can be configured to emit: i) a plurality of wavelengths of photons between about 620 nm and about 640 nm, ii) an intensity range between about 0.18 mW/cm2 and about 50 mW/cm2, optionally at about 30 mW/cm2; and iii) a radiant energy density range between about 0.05 J/cm2 and about 100 J/cm2. The electromagnetic energy source can also be configured to emit a plurality of wavelengths of photons for at least a duration of about 5 minutes to about 60 minutes. In certain embodiments of the device, the heat exchanger is a Peltier element.

Alternatively or additionally, in some particular embodiments, the circulated medium can be water or a gas, including, but not limited to, $CO_2$.

In a further aspect, the control circuit can be loaded with dosage presets on a storable medium, wherein the dosage presets are combinations of electromagnetic energy, intensity, and duration. In some embodiments of the DNA repair device, a control scheme further controls atmosphere and irradiation in conjunction with temperature.

Alternatively or additionally, in certain embodiments, the control circuit modulates the electromagnetic energy source to produce increasing and decreasing intervals of light emission. Alternatively or additionally, in some embodiments the modulation is at least one of pulsing, current limiting, voltage limiting, diffusing, or absorbing.

A method for repairing DNA is also provided herein. In one aspect, the method comprises, or consists essentially of, or yet further consists of, applying an electromagnetic energy to a plurality of biological cells, wherein the electromagnetic energy comprises a plurality of wavelengths of photons between about 620 nm and about 640 nm. The electromagnetic energy can be applied in a power range between about 0.18 mW/cm2 and about 50 mW/cm2 and for a duration between about 5 minutes to about 60 minutes. In certain embodiments, the electromagnetic energy can be in an intensity range between about 0.18 mW/cm2 and about 50 mW/cm2. In further embodiments, the electromagnetic energy can also be applied in a radiant energy density range between about 0.05 J/cm2 and about 100 J/cm2. The electromagnetic energy can comprise wavelengths appearing red on the visible spectrum.

In some embodiments of the method, a source of the electromagnetic energy comprises a light-emitting diode, an organic light emitting diode, a laser, or a fluorescent lamp. The plurality of biological cells can be separated from direct contact with the energy source by a temperature-controlled platform. The electromagnetic energy source also can be modulated to produce increasing and decreasing intervals of light emission. This modulation can be at least one of pulsing, current limiting, voltage limiting, diffusing, or absorbing.

The methods of this application can be applied to a plurality of biological cells, e.g. animal cells. In certain embodiments, the animal cells are mammalian cells such as bovine, feline, equine, canine, simian, rat, or human cells. The plurality of biological cells further can be at least one of normal cells, tumor cells, hyperproliferative cells, cancerous cells, somatic cells, stem cells. They can be primary cells from a tissue biopsy, cultured cells or cells from a cell culture line, and/or a living cell culture. In one aspect, the cells comprise Ethynyl-2'-deoxyuridine (EdU) and/or γ-H2AX. In one aspect of the disclosure exposure to the electromagnetic energy can increase at least one of Ethynyl- 2'-deoxyuridine (EdU) or γ-H2AX in the plurality of biological cells. The presently disclosed method can repair at least one of oxidative damage or UV damage to DNA.

Also provided herein is a method of DNA repair comprising, or consisting essentially of, or yet further consisting of inserting a plurality of biological cells into a device as described herein, and applying an electromagnetic energy to the plurality of biological cells, wherein the electromagnetic energy comprises a plurality of wavelengths of photons between about 620 nm and about 640 nm, and further wherein the electromagnetic energy is applied in a power range between about 0.18 mW/cm$^2$ and about 50 mW/cm$^2$ and for a duration between about 5 minutes to about 60 minutes. In certain embodiments, the animal cells are mammalian cells such as bovine, feline, equine, canine, simian, rat, or human cells. The plurality of biological cells further can be at least one of normal cells, tumor cells, hyperproliferative cells, cancerous cells, somatic cells, stem cells. They can be primary cells from a tissue biopsy, cultured cells or cells from a cell culture line, and/or a living cell culture. In one aspect, the cells comprise Ethynyl-2'-deoxyuridine (EdU) and/or γ-H2AX. In one aspect of the disclosure exposure to the electromagnetic energy can increase at least one of Ethynyl-2'-deoxyuridine (EdU) or γ-H2AX in the plurality of biological cells. The presently disclosed method can repair at least one of oxidative damage or UV damage to DNA.

DETAILED DESCRIPTION

Before the compositions and methods are described, it is to be understood that the disclosure is not limited to the particular methodologies, protocols, cell lines, assays, and reagents described, as these may vary. It is also to be understood that the terminology used herein is intended to describe particular embodiments of the present disclosure, and is in no way intended to limit the scope of the present disclosure as set forth in the appended claims.

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present disclosure, the preferred methods, devices, and materials are now described. All technical and patent publications cited herein are incorporated herein by reference in their entirety. Nothing herein is to be construed as an admission that the disclosure is not entitled to antedate such disclosure by virtue of prior disclosure.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about".

A. Definitions

As used in the specification and claims, the singular form "a", "an" and "the" include plural references unless the context clearly dictates otherwise. For example, the term "a cell" includes a plurality of cells, including mixtures thereof.

As used herein, the term "about" is used to indicate that a value includes the standard deviation of error for the device or method being employed to determine the value. The term "about" when used before a numerical designation, e.g., temperature, time, amount, and concentration, including range, indicates approximations which may vary by (+) or (−) 15%, 10%, 5%, 3%, 2%, or 1%.

As used herein, "and/or" refers to and encompasses any and all possible combinations of one or more of the associated listed items, as well as the lack of combinations when interpreted in the alternative ("or").

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this disclosure or process steps to produce a composition or achieve an intended result. Embodiments defined by each of these transition terms are within the scope of this disclosure.

The terms or "acceptable," "effective," or "sufficient" when used to describe the selection of any components, ranges, dose forms, etc. disclosed herein intend that said component, range, dose form, etc. is suitable for the disclosed purpose.

As used herein, a "cancer" is a disease state characterized by the presence in a subject of cells demonstrating abnormal uncontrolled replication and can be used interchangeably with the term "tumor." In some embodiments, the cancer is a skin cancer, basal cell carcinoma, squamous cell carcinoma, melanoma, and/or non-melanoma, solid tumor, lung cancer, liver cancer, kidney cancer, brain cancer, colorectal cancer, pancreatic cancer, bone cancer, throat cancer, lymphoma, or leukemia.

The term "cell" as used herein may refer to either a prokaryotic or eukaryotic cell, optionally obtained from a subject or a commercially available source. The cell can be in vitro or in vivo.

As used herein, "electromagnetic energy" is a form of energy that can be reflected or emitted from objects through electrical or magnetic waves traveling through space. Electromagnetic energy comes in a range of forms, including gamma rays, X-rays, ultraviolet radiation, visible light, microwaves, radio waves and infrared radiation.

As used herein, "oxidative damage" occurs when there is an imbalance between the production of free radicals and a subject's ability to counteract their damaging effects through neutralization with antioxidants. Oxidative damage is the harm sustained by cells and tissues that are unable to keep up with free radical production.

As used herein, "Peltier element" refers to any of a cooler, heater, or thermoelectric heat pump that is a solid-state active heat device which transfers heat from one side of the device to the other, with consumption of electrical energy, depending on the direction of the current.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. When the disease is cancer, the following clinical end points are non-limiting examples of treatment: reduction in skin cancer, slowing of cancerous growths, longer overall survival, longer time to tumor progression, inhibition of metastasis or a reduction in metastasis of a tumor.

The presently disclosed device and methods can use red light of about 620 to about 640 nm in wavelength to trigger the repair and synthesis of DNA. Specifically, the disclosed technology can repair DNA damage, including damage resulting from UV and oxidative damage, and general DNA damage where no specific source can be identified. By implementing red light therapy in certain dosages, the disclosed device and methods of use can repair DNA in human and non-human animal subjects.

In some embodiments, the disclosed method and device administer red light therapy through an array of electromagnetic energy sources with radiant intensities between 180 μW/cm2 and 50 mW/cm2 and with dosage times between 5 minutes and 60 minutes. Dosage powers translate to an equivalent energy dosage of 0.05 J/cm2 to 100 J/cm2. In some embodiments, safe and effective combinations of intensities and dosage times of the red light therapy can be preset into the device and can be selectable and tunable by the user. The tissue under treatment can also be separated from direct contact with the LED array by an optically clear, and temperature controlled treatment platform.

The disclosed device can also contains methods to control conditions at a treatment platform to maintain ideal conditions for DNA repair at the location of therapy. The described invention controls the temperature at the location of therapy by circulating temperature controlled water through the surface of the treatment platform. A thermal sensor within the treatment platform gives exact temperature readings to a programmable central circuit which then activates a Peltier element to heat or cool the circulated medium which circulates through the treatment area. In some embodiments, the circulated medium is water. Controlling gas composition, such as % $CO_2$ or other conditions, at the location of therapy can be necessary depending on the technology's industrial or commercial applications. As such the active control, via sensor and actuation, of any medium in direct or proxy contact with the subject of treatment is contemplated within this embodiment.

Wavelength:

The wavelength range of about 620 nm to about 640 nm is unique within the realm of light therapy. Some existing art describes overly broad ranges of wavelengths claiming anything from blue to red and infrared; however, such art focuses on the form of device for administering light and not the wavelengths and/or dosage itself.

The specific wavelength can be about 620 nm, about 621 nm, about 622 nm, about 623 nm, about 624 nm, about 625 nm, about 626 nm, about 627 nm, about 628 nm, about 629 nm, about 630 nm, about 631 nm, about 632 nm, about 634 nm, about 635 nm, about 636 nm, about 637 nm, about 638 nm, about 639 nm, or about 640 nm.

Dosage:

The disclosed methods utilize a specific wavelength range at higher intensities, and longer exposures to specifically achieve DNA repair and DNA synthesis than previously disclosed methods. In certain embodiments, the specific dosages include intensity of between about 0.18 mW/cm$^2$ up to about 50 mW/cm$^2$ on the about 620 nm to about 640 nm wavelength. The intensity can be about 0.18 mW/cm$^2$, 1 mW/cm$^2$, 2 mW/cm$^2$, 3 mW/cm$^2$, 4 mW/cm$^2$, 5 mW/cm$^2$, 6 mW/cm$^2$, 7 mW/cm$^2$, 8 mW/cm$^2$, 9 mW/cm$^2$, 10 mW/cm$^2$, 11 mW/cm$^2$, 12 mW/cm$^2$, mW/cm$^2$, 13 mW/cm$^2$, 14 mW/cm$^2$, 15 mW/cm$^2$, 16 mW/cm$^2$, 17 mW/cm$^2$, 18 mW/cm$^2$, 19 mW/cm$^2$, 20 mW/cm$^2$, 21 mW/cm$^2$, 22 mW/cm$^2$, 23 mW/cm$^2$, 24 mW/cm$^2$, 25 mW/cm$^2$, 26 mW/cm$^2$, 27 mW/cm$^2$, 28 mW/cm$^2$, 29 mW/cm$^2$, 30 mW/cm$^2$, 31 mW/cm$^2$, 32 mW/cm$^2$, 33 mW/cm$^2$, 34 mW/cm$^2$, 35 mW/cm$^2$, 36 mW/cm$^2$, 37 mW/cm$^2$, 38 mW/cm$^2$, 39 mW/cm$^2$, 40 mW/cm$^2$, 41 mW/cm$^2$, 42 mW/cm$^2$, 43 mW/cm$^2$, 44 mW/cm$^2$, 45 mW/cm$^2$, 46 mW/cm$^2$, 47 mW/cm$^2$, 48 mW/cm$^2$, 49 mW/cm$^2$, 50 mW/cm$^2$.

Duration:

The duration of treatment can be about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes.

B. Device

Referring to FIGS. 1 and 2, a DNA repair device in accordance with the principles of the present disclosure is described.

The present disclosure overcomes the drawbacks of previously-known devices and methods. FIGS. 1 and 2 show an example DNA repair device 10 having a housing 100 including at least a top side 102. The top side 102 of the housing 100 defines an opening 106. A fillable, translucent platform 108 is coupled to the top side 102 of housing 100. Platform 108 can be configured to be translucent (i.e., optically clear) so that electromagnetic energy may pass through both the medium (e.g., a gaseous medium) and also through platform 108 and contact a biological tissue. The platform is 108 situated between the opening 106 and an array 110 disposed within the housing 100. The array 110 comprises a plurality of electromagnetic energy sources 112. A thermal sensor 114 is coupled to the platform 108. A heat exchanger 116 is disposed within the housing 100 and is operatively coupled to a fluid pump 118. The heat exchanger 116 is configured to heat or cool a medium in the fluid pump 118. The fluid pump 118 is configured to circulate the medium to the fillable platform 108. A control circuit 120 is disposed within the housing 100 and is operatively coupled to at least one of the thermal sensor 114, the array 110, the heat exchanger 116, and the fluid pump 118.

In some embodiments, the control circuit 120 is a programmable input device. In certain embodiments, the input device is controlled by a user-activated tunable knob 124. Moreover, the pump 118 further can include a circulation loop 126 in fluid communication with the fillable platform 108.

The electromagnetic energy sources 112 of the device 10 can be at least one of a light-emitting diode, an organic light emitting diode, a laser, or a fluorescent lamp. The electromagnetic energy source 112 can be configured to emit: i) a plurality of wavelengths of photons between about 620 nm and about 640 nm, ii) an intensity range between about 0.18 mW/cm$^2$ and about 50 mW/cm$^2$, optionally at about 30 mW/cm$^2$; and iii) a radiant energy density range between about 0.05 J/cm$^2$ and about 100 J/cm$^2$. The electromagnetic energy source 112 can also be configured to emit a plurality of wavelengths of photons for at least a duration of about 5 minutes to about 60 minutes. The electromagnetic energy sources In certain embodiments of the device, the heat exchanger 116 is a Peltier element. In some particular embodiments, the circulated medium can be water, gas, or $CO_2$. The control circuit 120 can be loaded with dosage presets on a storable medium, wherein the dosage presets are combinations of electromagnetic energy, intensity, and duration. In some embodiments of the DNA repair device, a control scheme further controls atmosphere and irradiation in conjunction with temperature.

In some particular embodiments, the electromagnetic energy source 112 is modulated to produce increasing and decreasing intervals of light emission. In more particular embodiments, the modulation is at least one of pulsing, current limiting, voltage limiting, diffusing, or absorbing.

The DNA repair device can include a housing having at least a top side. The top side of the housing further can include an opening. In some embodiments, a fillable, translucent platform can be coupled to the top side of the housing, with the platform situated between the opening and an array disposed within the housing. In certain embodiments, the array can be a plurality of sources of electromagnetic energy. A thermal sensor can be coupled to the platform. A heat exchanger can be disposed within the housing and operatively coupled to a fluid pump. The heat exchanger can be configured to heat or cool a medium in the fluid pump, and the pump can then circulate the medium to the fillable platform. A control circuit can also be disposed within the housing and operatively coupled to one or more of the thermal sensor, the array, the heat exchanger, and the fluid pump. Alternatively or additionally, in some embodiments heat exchanger 116, array 110, and control circuit 120 may be in parallel or substantially in parallel.

In some embodiments, the control circuit is a programmable input device. The control circuit can also be controlled by a user-activated tunable knob. The pump can also be operably connected and in fluid communication with a circulation loop attached to the fillable platform. The electromagnetic energy sources can be at least one of a light-emitting diode, an organic light emitting diode, a laser, or a fluorescent lamp. The electromagnetic energy source can be configured to emit a plurality of wavelengths of photons between about 620 nm and about 640 nm. The electromagnetic energy source further can be configured to emit a plurality of wavelengths of photons in an intensity range between about 0.18 mW/cm$^2$ and about 50 mW/cm$^2$. In some embodiments, the electromagnetic energy source is configured to emit a plurality of wavelengths of photons at about 30 mW/cm$^2$. The electromagnetic energy sources can also be configured to emit a plurality of wavelengths of photons for at least a duration of about 5 minutes to about 60 minutes.

In some embodiments, the electromagnetic energy source can also be modulated to produce increasing and decreasing intervals of light emission. The modulation can be at least one of: pulsing, current limiting, voltage limiting, diffusing, or absorbing. As noted above, the electromagnetic energy source also can be configured to supply a radiant energy density range between about 0.05 J/cm$^2$ and about 100 J/cm$^2$.

In some embodiments, the heat exchanger can be a Peltier element. In other embodiments, the medium circulated through the device can be water or gas. In some embodiments, the circulated medium is $CO_2$. As shown in FIG. 6, the device can further include an operatively coupled power supply 128.

In some embodiments, the control circuit can be loaded with dosage presets on a storable medium. The dosage presets can be combinations of electromagnetic energy intensity and duration, and also can include a control scheme that further controls atmosphere and irradiation in conjunction with temperature.

C. Methods

An exemplary method in accordance with the principles of the present disclosure are also described. In one aspect, the methods of this disclosure are performed by use of the platform as described herein. The method of DNA repair comprises applying an electromagnetic energy to a biological cell where the electromagnetic energy includes a plurality of wavelengths of photons between about 620 nm and about 640 nm applied in a power range between about 0.18 mW/cm$^2$ and about 50 mW/cm$^2$ and for a duration between about 5 minutes to about 60 minutes. 3

Referring again to FIG. 3, the sources of electromagnetic energy can be an array comprising at least one of light-emitting diodes, organic light emitting diodes, lasers, or fluorescent lamps. The biological tissue can be separated from direct contact with the source by a temperature-controlled platform, as disclosed above. The electromagnetic energy source can also be modulated to produce increasing and decreasing intervals of light emission. In some embodiments, the modulation is pulsing. In other embodiments, the modulation is at least one of current limiting, voltage limiting, diffusing, or absorbing. The electromagnetic energy can be wavelengths appearing red on the visible spectrum.

A treated cell can be an animal cell. In other embodiments, the cell can be a human cell. Alternatively or additionally, in some embodiments the plurality of biological cells includes cancer cells. Exposure to the electromagnetic energy can increase Ethynyl-2'-deoxyuridine (EdU) in the cell, which can be used to assay DNA synthesis. Exposure to the electromagnetic energy can also increase γ-H2AX in the cell. In some embodiments of the method, the cell is a living cell culture. The method can also be used to repair oxidative damage to DNA. In some embodiments, the method can repair UV damage to DNA. In some embodiments of the method, DNA repair comprises cosmetic skin repair. The cell to be treated can also be a somatic cell or a stem cell. The methods of this application can be applied to a plurality of biological cells, e.g. animal cells. In certain embodiments, the animal cells are mammalian cells such as bovine, feline, equine, canine, simian, rat, or human cells. The plurality of biological cells further can be at least one of normal cells, tumor cells, hyperproliferative cells, cancerous cells, somatic cells, stem cells. They can be primary cells from a tissue biopsy, cultured cells or cells from a cell culture line, and/or a living cell culture. In one aspect, the cells comprise Ethynyl-2'-deoxyuridine (EdU) and/or γ-H2AX.

Figure 7:
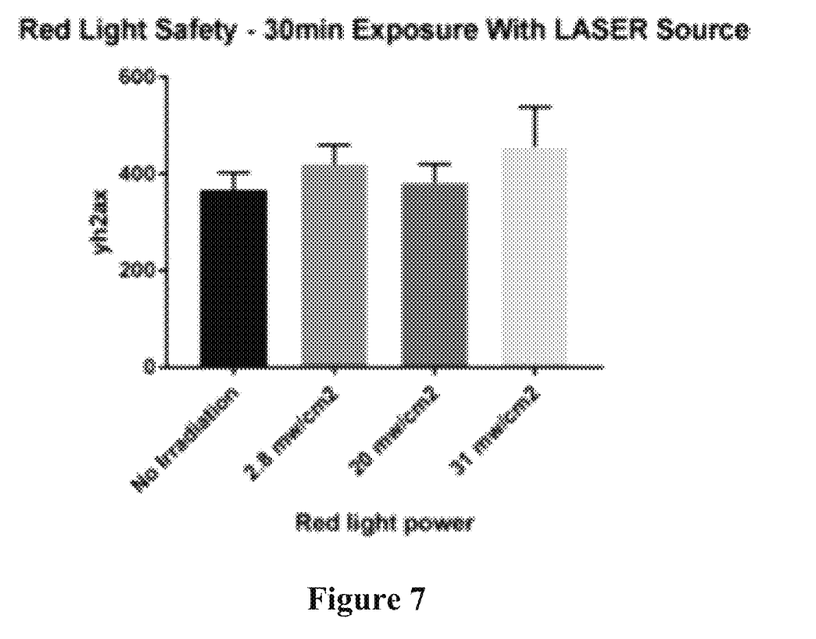
FIG. 7 shows an exemplary plot of the safe levels of red light exposure in relation to DNA damage.

The presently disclosed method can repair at least one of oxidative damage or UV damage to DNA. Thus, this disclosure provides a platform and a method to accomplish each of these purposes. Referring to FIG. 7, red light irradiation does not inflict significant damage and indeed can have restorative effects up to 31 mW/cm$^2$, as indicated by γ-H2AX levels. The methods of the present disclosure expose the plurality of biological cells to red light irradiation therapy in a safe and controlled manner by delivering irradiative electromagnetic energy in controlled doses and in an intensity range that lead to elevated levels of EdU and therefore has stronger DNA repair response compared to no treatment.

In particular embodiments, the electromagnetic energy can be an intensity range between about 0.18 mW/cm$^2$ and about 50 mW/cm$^2$. The electromagnetic energy can also be applied in a radiant energy density range between about 0.05 J/cm$^2$ and about 100 J/cm$^2$.

Figure 3:
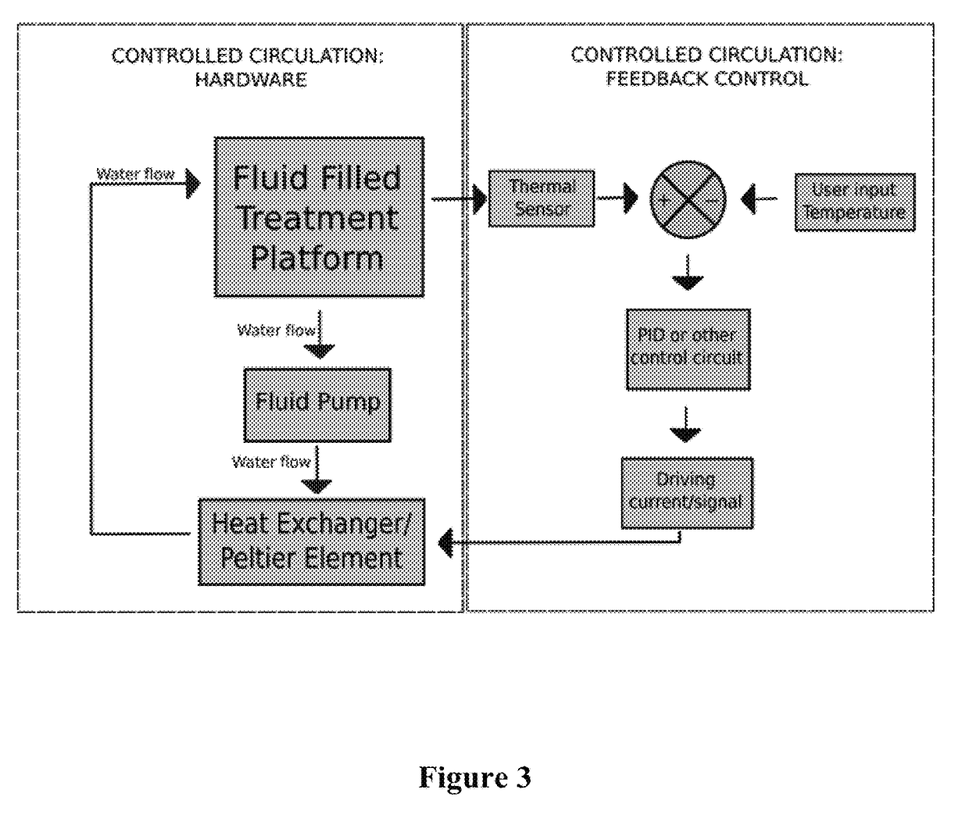
FIG. 3 illustrates a schematic view of a temperature controlled DNA repair device with circulated media.
Figure 4:
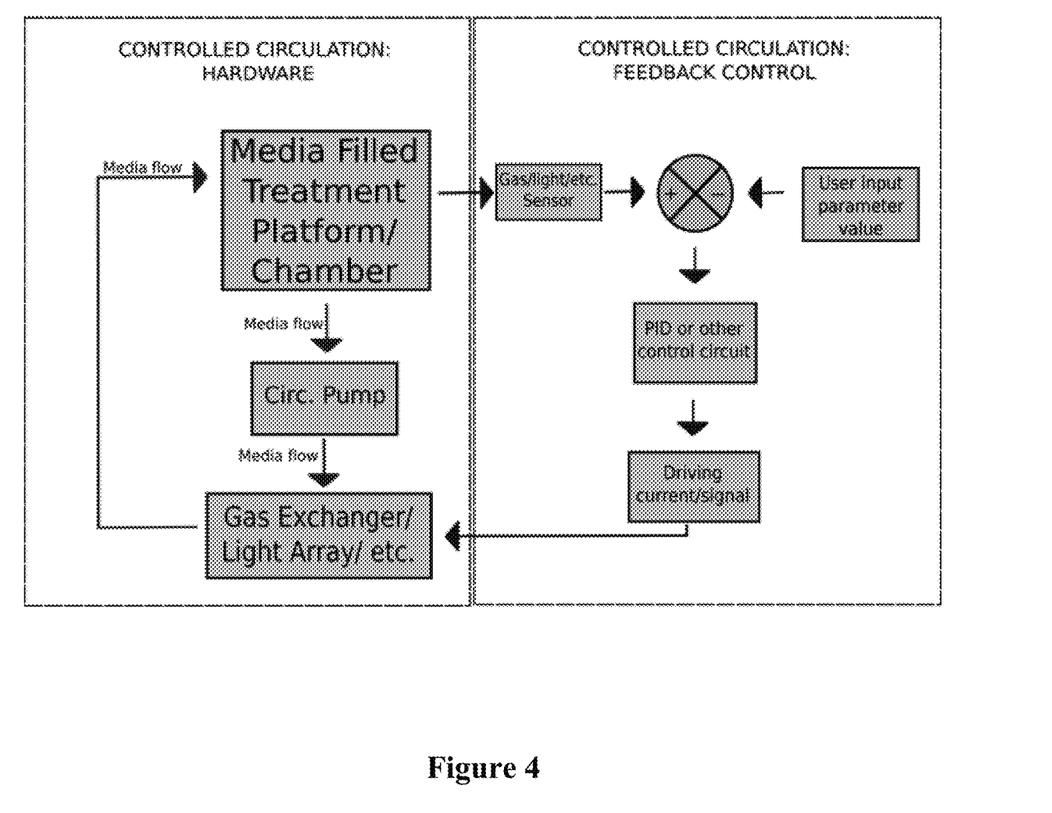
FIG. 4 illustrates a schematic view of a parameter controlled DNA repair device with circulated media.

FIG. 3 illustrates a schematic of an embodiment of the temperature controlled treatment platform with circulated fluid throughout the device. A user can input a particular temperature in the feedback control element of the device, which in turn actuates the control circuit, thereby driving a current or signal to the heat exchanger. The heat exchanger may be a Peltier element, as discussed above. The fluid pump then circulates a medium, such as water, to the fluid filled treatment platform. In one embodiment, the active sensing and control scheme in combination with media circulation is enacted to control temperature. Specifically, the treatment area may include thermal sensor 114 which provides temperature feedback to control circuit 120, which in turn modulates a heating or cooling module, such as heat exchanger 116. The temperature of platform 108 is regulated through the medium controlled heat exchange. The heated/cooled medium (e.g., water) is circulated by fluid pump 118 through the treatment area to maintain temperature. Referring now to FIG. 4, a user inputs a parameter via feedback control. Thus, control circuit 120 drives a current or signal to a gas exchanger or array 110. The amount of media flow will then determine the degree to which pump 118 further circulates the media. FIG. 4 shows a similar control scheme to FIG. 3, however this schematic maintains ideal atmosphere, irradiation, or other conditions at the treatment site Also provided herein is a method of DNA repair comprising, or consisting essentially of, or yet further consisting of inserting a plurality of biological cells into a device as described herein, and applying an electromagnetic energy to the plurality of biological cells, wherein the electromagnetic energy comprises a plurality of wavelengths of photons between about 620 nm and about 640 nm, and further wherein the electromagnetic energy is applied in a power range between about 0.18 mW/cm$^2$ and about 50 mW/cm$^2$ and for a duration between about 5 minutes to about 60 minutes. In certain embodiments, the animal cells are mammalian cells such as bovine, feline, equine, canine, simian, rat, or human cells. The biological tissue can be separated from direct contact with the source by a temperature-controlled platform, as disclosed above. The electromagnetic energy source can also be modulated to produce increasing and decreasing intervals of light emission. In some embodiments, the modulation is pulsing. Additionally or alternatively, in some embodiments, the modulation is at least one of current limiting, voltage limiting, diffusing, or absorbing. The electromagnetic energy can be wavelengths appearing red on the visible spectrum. The plurality of biological cells further can be at least one of normal cells, tumor cells, hyperproliferative cells, cancerous cells, somatic cells, stem cells. They can be primary cells from a tissue biopsy, cultured cells or cells from a cell culture line, and/or a living cell culture. In one aspect, the cells comprise Ethynyl-2'-deoxyuridine (EdU) and/or γ-H2AX. In one aspect of the disclosure exposure to the electromagnetic energy can increase at least one of Ethynyl-2'-deoxyuridine (EdU) or γ-H2AX in the plurality of biological cells. The presently disclosed method can repair at least one of oxidative damage or UV damage to DNA.

D. Experimental Results and Discussion

Figure 5:
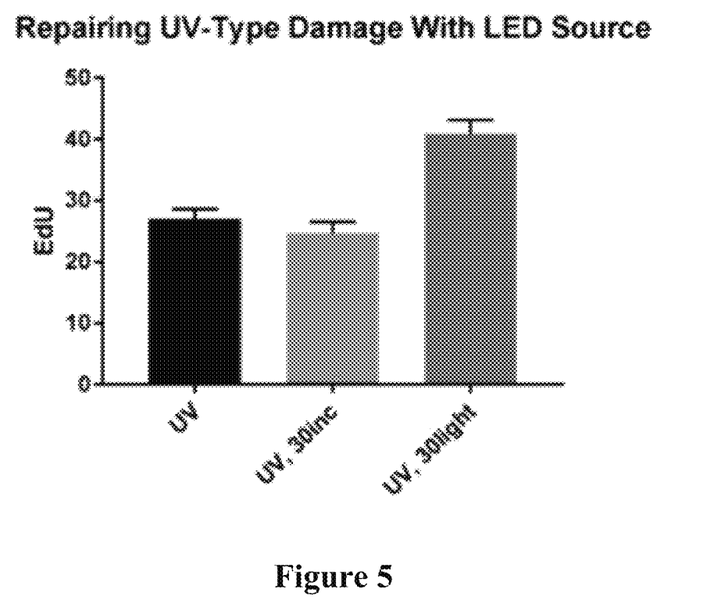
FIG. 5 shows an exemplary plot of UV damaged DNA repair findings using the disclosed device and methods.

FIG. 5 shows an exemplary plot of UV damaged DNA repair findings using the disclosed device to deliver red light therapy. The y-axis of the plot shows higher levels of 5-Ethynyl-2'-deoxyuridine (EdU). EdU is a thymidine analogue which is incorporated into the DNA of dividing cells, and is used to track proliferating cells in multiple biological systems. Here, higher EdU levels in the light treated group indicate that the 30 minute red light therapy increased the amount of DNA repair. Thus, the disclosed device successfully stimulated DNA repair in UV damaged DNA.

FIG. 7 illustrates a graph showing red light safety that helped spur early indications of the potential success of the presently claimed device and methods. The graph shows that red light irradiation does not inflict significant DNA damage, which is indicated by γ-H2AX levels in the treatment cells. γ-H2AX is a biomarker that is linked to DNA double strand breaks. The plot shows the amount of γ-H2AX up to 31 mW/cm$^2$ intensity.

Figure 8A:
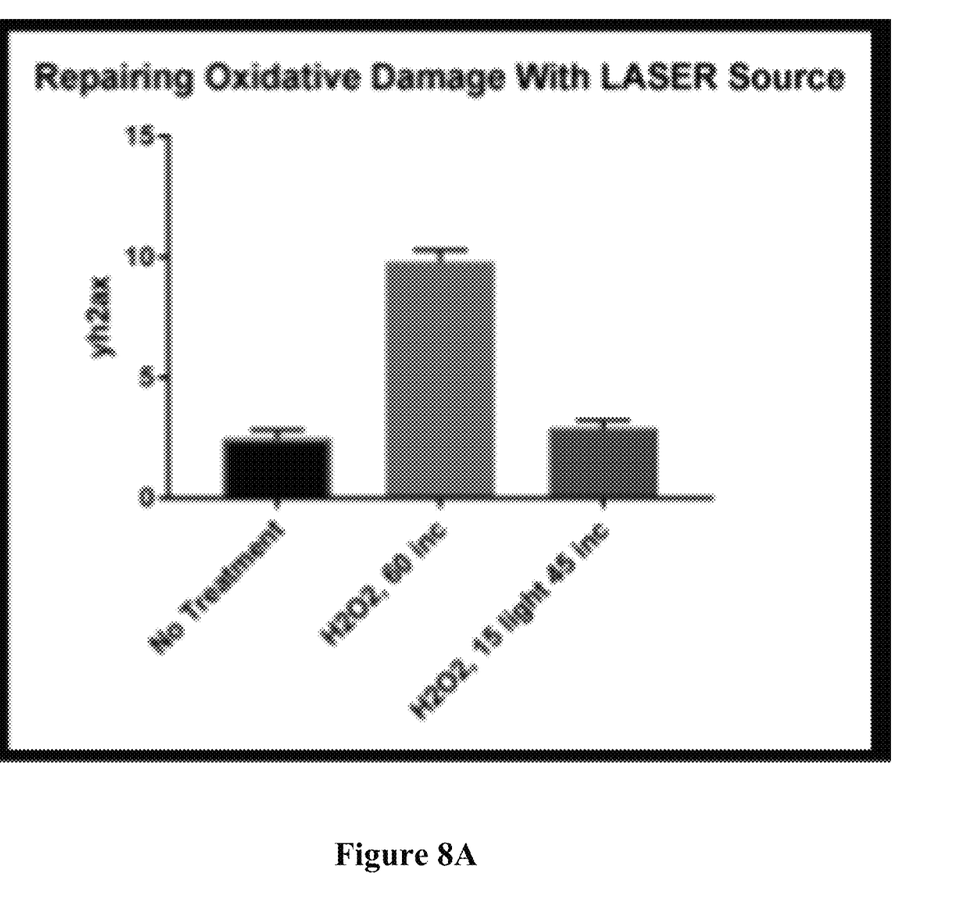
FIG. 8A shows an exemplary plot of repairing DNA with oxidative damage with a LASER source.
Figure 8B:
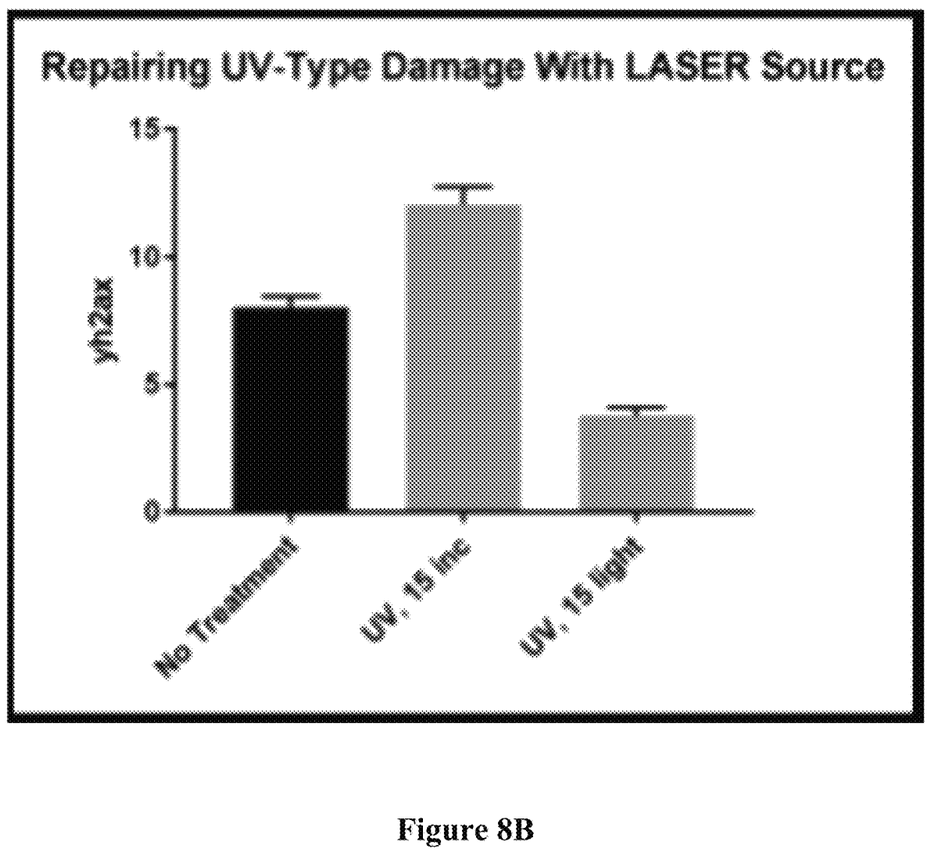
FIG. 8B shows an exemplary plot of repairing UV type damage with a LASER source.

FIG. 8A shows DNA repair in response to oxidative damage with LASER source. These findings indicate that oxidatively damaged DNA is restored to the normal levels of DNA damage, again depicted by the levels of γ-H2AX. Similar to FIG. 8A, FIG. 8B illustrates findings that UV damaged DNA, rather than oxidatively damaged DNA, is restored to lower levels of DNA damage, again indicated by levels of γ-H2AX, after 15 minutes of red light therapy.

E. Applications

Cosmetic Skin Treatment:

One application of the disclosed device and method is in the treatment of skin tissue for healing, protective, and regenerative effects. In some embodiments, self-administered light therapy could be incorporated into an "at home" device to treat the following indications: sunburn recovery, sunburn protection, reversing or preventing tissue/skin aging, stimulating tissue/skin repair, stimulating tissue/skin regeneration. This list is not exclusive and the possible skin treatments are not limited to the foregoing.

Cell and DNA Amplification:

The red light therapy and associated machinery needed to maintain ideal conditions can be utilized as a method in the industrial amplification of cell lines and stem cell lines. By adding this method to the process of cellular amplification, resulting genomes can be expected to have less damage, thereby increasing the genome quality, reproducibility, and viable yield.

The disclosed red light therapy and associated machinery can be incorporated into a laboratory scale device to repair accrued damage to existing and experimental cell lines. This can help to extend the longevity of laboratory cell lines and increase cell viability between cultures and laboratory scale cellular/tissue amplification.

Cancer:

Preliminary evidence would suggest that this therapy could be used to improve the effectiveness of some cancer treatments. Because the therapy and associated machinery can repair damaged DNA, this would at least in part, restore some natural genetic checkpoints and the related cell-death responses which some cancer treatments leverage to achieve their therapeutic effects.

F. Equivalents

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Additional information regarding the claimed embodiments is provided in the Appendix attached hereto.

Other aspects are set forth within the following claims.

What is claimed is:

1. A DNA repair device comprising:
   a housing comprising at least a top side and a bottom side, wherein the top side of the housing further comprises an opening;
   a fillable, translucent platform coupled to the top side of the housing, wherein the platform is situated between the opening and an array disposed within the housing, wherein the array comprises a plurality of electromagnetic energy sources;
   a thermal sensor coupled to the platform;
   a heat exchanger disposed within the housing and operatively coupled to a fluid pump, wherein the heat exchanger is configured to heat or cool a medium in the fluid pump, further wherein the fluid pump is configured to circulate the medium to the fillable platform; and
   a control circuit disposed within the housing and operatively coupled to at least one of the thermal sensor, the array, the heat exchanger, and the fluid pump.

2. The device of claim 1, wherein the control circuit is a programmable input device.

3. The device of claim 1, wherein the pump further comprises a circulation loop in fluid communication with the fillable platform.

4. The device of claim 1, wherein the electromagnetic energy sources comprise at least one of a light-emitting diode, an organic light emitting diode, a laser, or a fluorescent lamp.

5. The device of claim 1, wherein the electromagnetic energy source is configured to emit:
   i) a plurality of wavelengths of photons between about 620 nm and about 640 nm;
   ii) an intensity range between about 0.18 $mW/cm^2$ and about 50 $mW/cm^2$; and/or
   iii) a radiant energy density range between about 0.05 $J/cm^2$ and about 100 $J/cm^2$.

6. The device of claim 1, wherein the electromagnetic energy source is configured to emit a plurality of wavelengths of photons for at least a duration of about 5 minutes to about 60 minutes.

7. The device of claim 1, wherein the heat exchanger is a Peltier element.

8. The device of claim 1, wherein the circulated medium comprises water, gas, or $CO_2$.

9. The device of claim 1, wherein the control circuit is loaded with dosage presets on a storable medium, wherein the dosage presets comprise combinations of electromagnetic energy, intensity, and duration.

10. The device of claim 1, wherein a control scheme further controls atmosphere and irradiation in conjunction with temperature.

11. The device of claim 1, wherein the electromagnetic energy source is modulated to produce increasing and decreasing intervals of light emission, wherein the modulation is at least one of pulsing, current limiting, voltage limiting, diffusing, or absorbing.

12. A method of repairing DNA damage in a cell, the method comprising applying an electromagnetic energy to the device of claim 1, wherein the device comprises the cell.

13. The method of claim 12, wherein a source of the electromagnetic energy is an array further comprising at least one of a light-emitting diode, an organic light emitting diode, a laser, or a fluorescent lamp.

14. The method of claim 12, wherein the cell is separated from direct contact with an electromagnetic energy source by a temperature-controlled platform.

15. The method of claim 12, wherein the cell comprises an animal cell.

16. The method of claim 12, wherein the cell comprises a human cell.

17. The method of claim 12, wherein the cell is a somatic cell or a stem cell.

18. The method claim 12, wherein exposure to the electromagnetic energy increases at least one of Ethynyl-2'-deoxyuridine (EdU) or γ-H2AX in the cell.

19. The method claim 12, wherein the method is repairing at least one of oxidative damage or UV damage to DNA or wherein the method comprises cosmetic skin repair.

20. The method of claim 12, wherein the electromagnetic energy comprises:
   i) an intensity range between about 0.18 mW/cm$^2$ and about 50 mW/cm$^2$; and
   ii) is applied in a radiant energy density range between about 0.05 J/cm$^2$ and about 100 J/cm$^2$.

21. The method of claim 12, wherein the electromagnetic energy comprises wavelengths appearing red on the visible spectrum.

* * * * *